(12) United States Patent
Prems et al.

(10) Patent No.: US 12,217,837 B2
(45) Date of Patent: Feb. 4, 2025

(54) SYSTEMS AND METHODS FOR DIGITIZATION OF TISSUE SLIDES BASED ON ASSOCIATIONS AMONG SERIAL SECTIONS

(71) Applicant: Pramana, Inc., Cambridge, MA (US)

(72) Inventors: Jithin Prems, Dooravani Nagar (IN); Manish Shiralkar, Pune (IN); Prasanth Perugupalli, Cary, NC (US); Shilpa G. Krishna, Kerala (IN); Durgaprasad Dodle, Telangana (IN); Raghubansh Bahadur Gupta, Bangalore (IN); Jaya Jain, Shahpura (IN); Prateek Jain, Karnataka (IN); Priyanka Golchha, Rajasthan (IN)

(73) Assignee: Pramana, Inc., Cambridge, MA (US)

( * ) Notice: Subject to any disclaimer, the term of this patent is extended or adjusted under 35 U.S.C. 154(b) by 0 days.

(21) Appl. No.: 18/603,051

(22) Filed: Mar. 12, 2024

(65) Prior Publication Data
US 2024/0379197 A1 Nov. 14, 2024

Related U.S. Application Data

(60) Provisional application No. 63/465,032, filed on May 9, 2023.

(51) Int. Cl.
*G16H 10/40* (2018.01)
(52) U.S. Cl.
CPC .................................. *G16H 10/40* (2018.01)
(58) Field of Classification Search
CPC ..................................................... G16H 10/40
(Continued)

(56) References Cited

U.S. PATENT DOCUMENTS 8,880,351 B2 11/2014 Can et al.
9,818,190 B2 11/2017 Chukka et al.
(Continued)

FOREIGN PATENT DOCUMENTS

WO WO-2016107896 A1 * 7/2016 ........... G06T 7/0012
WO 2023081490 A1 5/2023

OTHER PUBLICATIONS

Li, Jiayun; Large-Scale Whole Slide Image Analysis with Deep Learning Methods to Improve Prostate Cancer Diagnosis; University of California, Los Angeles, ProQuest Dissertation & Theses, 2021. 28320855. (Year: 2021).*

(Continued)

*Primary Examiner* — Hiep V Nguyen
(74) *Attorney, Agent, or Firm* — Caldwell Intellectual Property Law

(57) ABSTRACT

The present disclosure describes an exemplary system and method for the digitization of tissue slides based on associations among serial sections. The system includes at least a computing device, wherein the computing device includes a memory and processor communicatively connected to one another, and a scanner, configured to scan a slide and send a digitized image of the slide to the computing device. A method for the digitization of tissue slides based on associations among serial sections may include receiving a candidate tissue map associated with a candidate tissue section, receiving a reference tissue map associated with a reference tissue section, aligning the candidate tissue map to the reference tissue map, comparing the aligned candidate tissue map to the reference tissue map, and generating a regenerated candidate tissue map as a function of the reference tissue map.

20 Claims, 9 Drawing Sheets

(58) Field of Classification Search
USPC .............................................................. 705/2
See application file for complete search history.

(56) References Cited

U.S. PATENT DOCUMENTS

| | | |
|---|---|---|
| 2013/0077892 A1 | 3/2013 | Ikeno et al. |
| 2014/0294266 A1 | 10/2014 | Eichhorn et al. |
| 2014/0354859 A1 | 12/2014 | Noyes et al. |
| 2021/0063288 A1* | 3/2021 | Mitra ................... G01N 1/2813 |
| 2021/0201536 A1 | 7/2021 | Atchison et al. |
| 2022/0156930 A1* | 5/2022 | Barnes .................. G06T 7/0012 |
| 2022/0189150 A1* | 6/2022 | Bentaieb ................ G16H 50/20 |
| 2023/0206434 A1 | 6/2023 | Anderson |

OTHER PUBLICATIONS

International Search Report; PCT/US2024/028323; Date: Oct. 25, 2024; By: Authorized Officer Shane Thomas.

* cited by examiner

SYSTEMS AND METHODS FOR DIGITIZATION OF TISSUE SLIDES BASED ON ASSOCIATIONS AMONG SERIAL SECTIONS

CROSS-REFERENCE TO RELATED APPLICATIONS

This application claims the benefit of priority of U.S. Provisional Patent Application Ser. No. 63/465,032, filed on May 9, 2023, and titled "SYSTEMS AND METHODS FOR DIGITIZATION OF TISSUE SLIDES BASED ON ASSOCIATIONS AMONG SERIAL SECTIONS," which is incorporated by reference herein in its entirety.

FIELD OF THE INVENTION

The present invention generally relates to the field of medical technology. In particular, the present invention is directed to systems and methods for digitization of tissue slides based on associations among serial sections.

BACKGROUND

Examination of slides containing biomedical specimens, such as tissue samples, under a microscope (e.g., an optical microscope) provides data that can be exploited for a variety of biomedical applications. For example, physicians and/or other qualified individuals may be able to diagnose pathological conditions or detect microbial organisms. In many instances, the physician may observe the slides directly under the microscope.

For medical diagnosis, Hematoxylin and Eosin (H&E) staining is used for viewing cellular and tissue structure detail by pathologists. Hematoxylin shows the ribosomes, chromatin within the nucleus, and other structures as a deep blue-purple color. Eosin shows the cytoplasm, collagen, connective tissue, and other structures that surround and support the cell as an orange-pink color. H&E staining helps identify different types of cells and tissues and provides important information about the pattern, shape, and structure of cells in a tissue sample. The variation of stain intensity is often driven by the pathologist's learning experience and personal preference. Because this stain demonstrates such a broad range of cytoplasmic, nuclear, and extracellular matrix features, H&E images are widely used in medical diagnosis.

With rapid development in digital technologies, users of pathology slides have moved to digitizing the slides. The digitization of pathology slides using automated microscopes involves assessing the tissue content of the slide and then scanning the slide at a high magnification. This scanning is restricted to only the content within the identified enclosing bounding box. Hence, the generation of a map of tissue regions on a tissue biopsy slide is accomplished, thereby enabling the acquisition of tissues.

During biopsy studies, patients are assigned a unique case identification number. Multiple tissue blocks associated with the unique case identification are extracted. In turn, each block of tissue is sliced into multiple thin slices that are then mounted on slides. Slices from the same tissue block are referred to as serial section. Each of the tissue slices may be stained and/or unstained to be assessed for tissue content. A user may then assess the tissue slices with imaging and image processing techniques.

The assessment of the tissue via serial section analysis is complicated by issues with debris, bubbles, annotations, scratches, and extra stain present on the slide. These issues may lead to the scanning of extra unwanted areas, resulting in an increase in scan time and file storage size. These issues decrease the time and data storage efficiency of the assessment. Likewise, these issues may also lead to some tissue content being missed due to faint staining, causing the analysis to be skewed.

SUMMARY OF THE DISCLOSURE

In an aspect systems and methods for digitization of tissue slides based on associations among serial sections may allow for an accurate automated serial section analysis. The digitization of tissue slides based on associations among serial sections may occur via a system including at least a computing device, having a processor and a memory, and a scanner configured to scan a slide and send a digitized image of the slide to the computing device.

In another aspect a method for digitizing tissue slides based on associations among serial sections may include receiving a candidate tissue map associated with a candidate tissue section, receiving a reference tissue map associated with a reference tissue section, aligning the candidate tissue map to the reference tissue map, comparing the aligned candidate tissue map to the reference tissue map, and generating a regenerated candidate tissue map as a function of the reference tissue map.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for digitization of tissue slides based on associations among serial sections. In an embodiment, the digitization of tissue slides based on associations among serial sections may occur via a system including at least a computing device, having a processor and a memory, and a scanner configured to scan a slide and send a digitized image of the slide to the computing device. In another aspect a method for digitizing tissue slides based on associations among serial sections may include receiving a candidate tissue map associated with a candidate tissue section, receiving a reference tissue map associated with a reference tissue section, aligning the candidate tissue map tot the reference tissue map, comparing the aligned candidate tissue map to the reference tissue map, and generating a regenerated candidate tissue map as a function of the reference tissue map.

Aspects of the present disclosure can be used to enable the acquisition of tissue content while avoiding debris, bubbles, annotations, and background stain. Aspects of the present disclosure can also be used to improve the accuracy of scanning of tissue specimen having various types, sizes, fragments, and/or stain level. This is so, at least in part, because when serial section slides are processed as a group, the analysis benefits from the minimization of issues related to individual slide tissue assessment. Exemplary embodiments illustrating aspects of the present disclosure are described below in the context of several specific examples.

Figure 1:
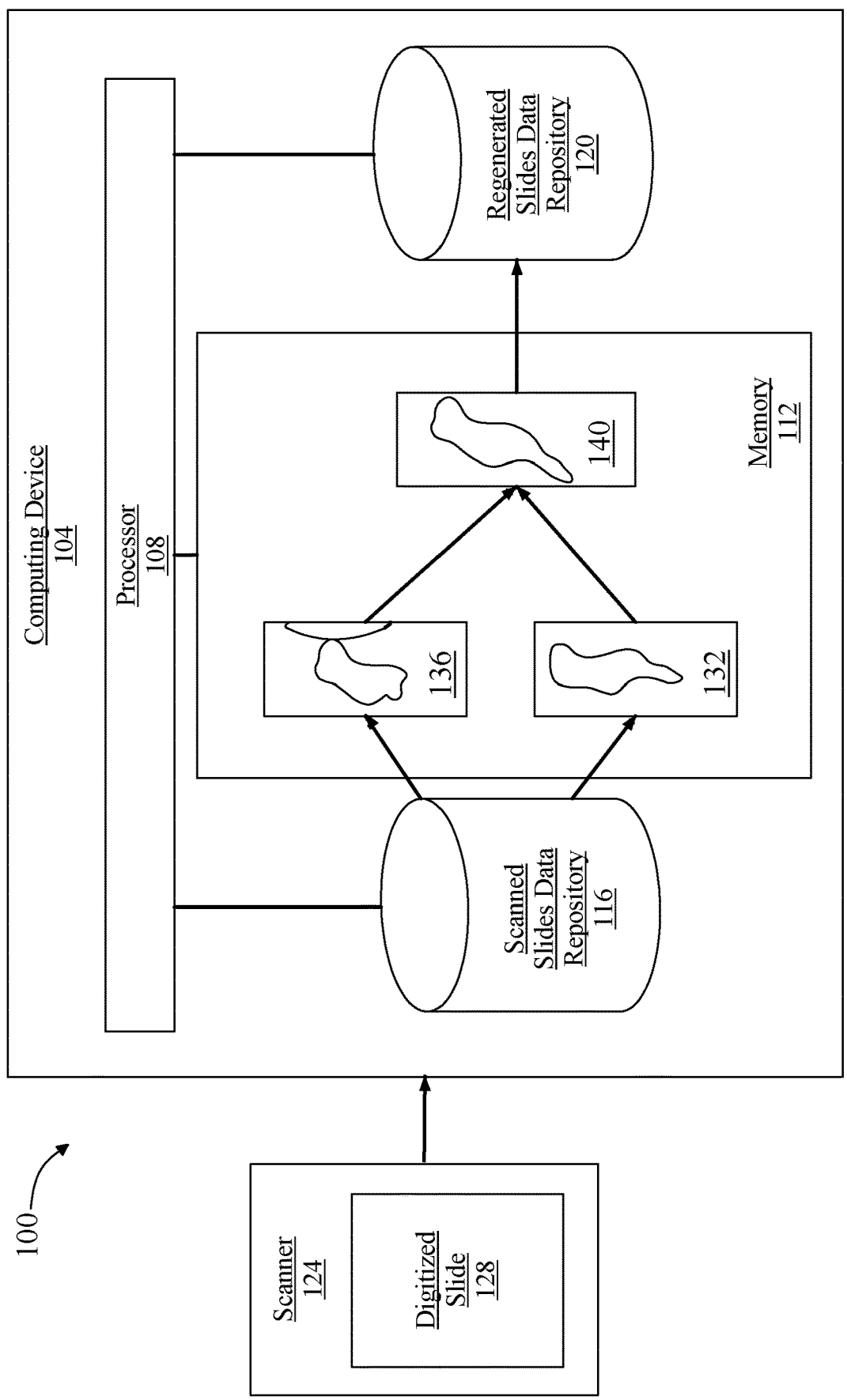
FIG. 1 is a simplified diagram illustrating an exemplary system for slide digitization, in accordance with some embodiments.

Referring now to FIG. 1, an exemplary embodiment of a system for digitization of tissue slides based on associations among serial sections is illustrated. A system for digitization of tissue slides based on associations among serial sections may include at least a computing device 104 and scanner 124 configured to scan a slide and send a digitized image of the slide to computing device 104. Wherein computing device 104 further includes processor 108 and memory 112 communicatively connected to processor 108, wherein memory 112 has stored instructions configuring processor 108 to retrieve a candidate tissue map associated with a candidate tissue section, retrieve a reference tissue map associated with a reference tissue section, align candidate tissue map to reference tissue map, compare aligned candidate tissue map to reference tissue map, and generate a regenerated candidate tissue map as a function of reference tissue map. This may be implemented in part, without limitation, as disclosed in U.S. application Ser. No. 18/428,823, filed on Jan. 31, 2024 and entitled "SYSTEMS AND METHODS FOR VISUALIZATION OF DIGITIZED SLIDES" the entirety of which is incorporated herein by reference. In some embodiments, computing system may further include one or more storage devices. For example, and without limitation, scanned slides data repository 116 and/or regenerated slides data repository 120. "Digitization," as used throughout this disclosure, is the conversion of text, pictures, and/or sound into a digital form that can be processed by a computer. This may be implemented, without limitation, as disclosed in U.S. App. No. 63/466,950, filed on May 16, 2023 and entitled "SYSTEMS AND METHODS FOR INLINE QUALITY CONTROL OF SLIDE DIGITIZATION" the entirety of which is incorporated herein by reference. Further, this may be enhanced, without limitation, as disclosed in U.S. application. Ser. No. 18/227,155, filed on Jul. 27, 2023 and entitled "METHOD AND AN APPARATUS FOR INLINE IMAGE SCAN ENRICHMENT" the entirety of which is incorporated herein by reference. As used throughout this disclosure, "serial sections," refer to any series of sections cut in sequence from a prepared specimen. Additionally, a "repository," as used in this disclosure, is a receptable where things are or may be stored. In the instance of scanned slides data repository 116 and/or regenerated slides data repository 120, each repository respectfully, may store and or be accessed for the information it holds.

With further reference to FIG. 1, system 100 may include device 104 and scanner 124 communicatively connected to device 104. In an embodiment, device 104 may include a computing device and/or system in any embodiment as described throughout this disclosure. As a nonlimiting example, device 104 may include a personal computer, an on-premises server, a cloud-based server, and/or the like. In an embodiment, scanner 124 may include devices and/or systems used to digitize slides containing biomedical specimens, for example tissue samples. Such devices and/or systems may be any device and/or system as described throughout this disclosure. For example, and without limitation scanner 124 may include digital cameras, digital microscopes, digital pathology scanners, and/or the like. Device 104 and scanner 124 may communicate via a wired and/or wireless link, and/or via a network, including but not limited to one or more local area networks (LANs), wide area networks (WANs), wired networks, wireless networks, the Internet, and/or the like. Alternatively, in some embodiments, device 104 may be directly connected to and/or integrated within scanner 124. Each of these descriptions are exemplary and may be substituted with any other embodiment as described in further detail throughout this disclosure.

Still referring to FIG. 1, scanner 124 may be configured to capture digital image 128, which may be referred to throughout this disclosure as digitized slide 128. Digitized slides 128 may include any image produced using a digital camera and that may be stored as an electronic file. Some examples of this may include binary, grayscale, color, and/or multispectral images. Following digitization of the slide, scanner 124 may send digital image 128 as a digital file and/or data to device 104 via communicative link between scanner 124 and device 104.

With further reference to FIG. 1, device 104 may include processor 108 coupled to memory 112. Memory 112 may store instructions and/or data configuring processor 108 to perform specific operations. When operations are executed by processor 108, processor 108 may perform operations associated with the inline registration of serial sections and more specifically the generation of maps of tissue regions. Processor 108 may also be in communication with scanned slide data repository 116 and/or regenerated slides data repository 120. Processor 108 may be further configured to read, write, and/or manage data stored in scanned slides data repository 116 and regenerated slides data repository 120. Scanned slides data repository 116 stores data of digitized slides 128 from scanners, such as scanner 124. Stored data may include image data and/or meta data, such as case identification numbers and/or block identification numbers corresponding to the image data. In some embodiments, scanned slides data repository 116 and/or regenerated slides data repository 120 may be located in another device and/or a device that is separate from device 104. In an embodiment, device 104 may be configured to communicate with the separate device via a wired and/or wireless link, and/or via a network including one or more local area networks (LANs), wide area networks (WANs), wired networks, wireless networks, the Internet, and/or the like.

Continuing to reference FIG. 1, in an embodiment slide digitization may include the retrieval of candidate slides and reference slides identified based on stain information of slides under assessment. In some embodiments, identification of candidate slides and/or reference slides may automatically be accomplished real-time alongside the digitization process by an inline computer program executed by processor 108. An "inline computing program," refers to a computing term where code or data is inserted directly into its appropriate place within a larger block of code, rather than being called from a separate location. Alternatively, in some embodiments, identification of candidate slides and/or reference slides may be manually performed by a user. The identified candidate slide may be associated with information sufficient to identify one or more other slides from the same serial section set, which may be used as the reference slide. For example, and without limitation, candidate slide may have a corresponding case identification number and block identification number. Based on the case identification, as well as stain information of slides having the corresponding case identification number and the block identification number, another slide corresponding to the case identification number and the block identification number may be identified as a reference slide.

Further referencing FIG. 1, in some embodiments identified reference slides may be an H&E-stained slide. In contrast, identified candidate slide may be a non-H&E-stained slide. For example, and without limitation non-H&E-stained slides may be stained with Immunohistochemistry (IHC). IHC staining combines anatomical, immunological, and biochemical techniques to image discrete components in tissues by using appropriately labeled antibodies to bind specifically to their target antigens in situ. IHC staining makes it possible to visualize and document high-resolution distribution and localization of specific cellular components within cells and within their proper histological context. In some embodiments, identified reference slide may be a non-H&E-stained slide. When multiple candidate slides are identified, there may be any combination of a certain number of non-H&E-stained slides and a certain number of H&E-stained slides.

Continuing to reference FIG. 1, processor 108 may be configured to retrieve image data of reference slide and image data of candidate slide from scanned slides data repository 116 to memory 112. The described retrieval operation by processor 108 may be based on the case identification number and the block identification number of candidate slide, which have been supplied to processor 108. Using image data of reference slide and image data of candidate slide, processor 108 generates reference tissue map file 132 and candidate tissue map file 136, respectively. Reference tissue map file 132 may contain data of the tissue map of candidate slide.

With further reference to FIG. 1, in some embodiments, a user may identify a reference serial section and at least one non-reference serial action, otherwise described as a candidate serial section, on the same slide based on information such as shape and/or other attributes of the serial sections. The slide is also referred to as an intra-serial sections slide. In turn, reference tissue map file 132 may be generated by processor 108 from image data of reference serial section and candidate tissue map file 136 may be generated by processor 108 from image data of candidate serial section.

Continuing to reference FIG. 1, processor 108 may additionally be configured to align candidate tissue map file 136 with reference tissue map file 132. During this alignment process, candidate tissue map file 136 may be registered by processor 108 with the reference map file by leveraging information such as similarities of shape and size between mapped serial sections. For example, and without limitation, processor 108 may execute a registration module containing instructions stored in memory 112 to process candidate tissue map and reference tissue map. Processor 108 orients candidate tissue map, which may be stored in candidate tissue map file 136, to maximize the overlap between regions of interest identified in candidate tissue map and reference tissue map, which may be stored in reference tissue map file 132. Features used to align tissue maps may include tissue boundaries, contours, and/or other features that are visible in a slide, even in cases where such features may appear faint. The registration module may align one or more features that are common between candidate tissue map and reference tissue map. This may be accomplished by maximizing the overlap between common features in two or three dimensions in both tissue maps. Common features may include features that are detectable, such as without limitation, features discernable using automated computer vision techniques. Maximizing overlap may be achieved by applying one or more matrix transformations, such as, without limitation, rotating, translating, scaling and/or skewing, to candidate tissue map and/or reference tissue map.

With further reference to FIG. 1, processor 108 may be further configured to compare candidate tissue map file 136 with reference tissue map file 132 regarding properties such as shapes and sizes between mapped serial sections. In an embodiment, when a difference in compared properties is located as result of the comparison, differences are then utilized as correction factors to generate regenerated candidate tissue maps. In some embodiments, this process may include an initial step of generating a reference binary mask from reference tissue map and a candidate binary mask from candidate tissue map. These binary masks may identify the presence or absence of tissue across the slide in contrast to tissue maps which may provide a more detailed representation of the features on the slide. For example, and without limitation, binary masks may appear in a black and white format in contrast to RGB color format of features contained on a given slide. Reference binary mask and candidate binary mask may be aligned based on results of the alignment process as described above. For example, and without limitation, by applying matrix transformations determined by the registration module. Once aligned, adjustments may be made to candidate binary mask based on reference binary mask, resulting in a corrected candidate binary mask. As a nonlimiting example of this, a region of candidate binary mask originally identified as having no tissue present may be identified as having tissue in corrected candidate binary mask when the reference binary mask indicates that tissue is present in the region. Similarly, regions of candidate binary mask originally identified as having tissue present may be identified as having no tissue in corrected candidate binary mask when reference binary mask indicates that no tissue is present in the region. The corrected candidate binary mask may then be applied onto candidate tissue map, and candidate tissue map may be regenerated accordingly with corrections. Consequently, in some embodiments, the area of regenerated candidate tissue map where tissue is determined to be present is substantially equal to the corresponding area of reference tissue map.

Continuing to reference FIG. 1, these and other factors may be streamlined by instantiation of a machine learning module and/or a neural network. Training data that may be used to train machine-learning model and/or neural network may include exemplary input data, such as without limitation, digitized slide 128 data, such as without limitation class identification numbers, and/or block identification numbers, and/or the like, candidate tissue map data, reference tissue map data, regenerated candidate tissue map data, binary maps of any tissue map data, and/or the like, where each such example may be correlated to additional exemplary output data such as, without limitation, regenerated candidate tissue map data, and/or the like. Training of the model and/or network may take place either at device 104 and/or remotely. In the latter case, the model and/or network may be deployed at or by device 104 in any manner as described in this disclosure. In some embodiments, the machine-learning model and/or neural network may be trained remotely and then transmitted device 104, the model and/or network may be deployed at or device 104 in any manner described in this disclosure. Additionally, in some embodiments, the machine-learning model and or neural network may be updated to device 104, the model and/or network may be deployed at or by device 104 in any manner as described in this disclosure. The machine-learning model and/or network may be deployed/instantiated once trained in any form as described within this disclosure. Feedback from the deployment of the machine-learning model and/or neural network may be turned into new training data, which may be stored either locally and/or transmitted to another device and used for retraining of the model and/or network. Retraining may be administered either remotely or at device 104. Following retraining of the model and/or network, redeployment/instantiation may be accomplished at or by device 104 in any manner as described within this disclosure.

Further referencing FIG. 1, a regenerated candidate tissue map may be stored in a regenerated candidate tissue map file 140, which may be used by downstream applications such as further processing, data storage, and/or high-resolution scanning with large magnification multiples. Regenerated slides data repository 120 may store data of regenerated candidate tissue map. In an embodiment, as described throughout this disclosure, this may be referred to as regenerated candidate tissue map file 140. In some embodiments, binary masks and tissue maps generated during the process of slide digitization are configured to be low resolution without large magnification multiples.

With continued reference to FIG. 1, generating regenerated candidate tissue maps in an inline manner, as described above, may have various advantages. For example, candidate tissue map may be generated based on an image of a slide captured by scanner 124 at a low magnification, such as 1× magnification, and regenerated candidate tissue map may be generated prior to removing slide from scanner 124. In turn, scanner 124 may be instructed to carry out higher resolution scanning, such as 40× magnification, of specified regions of interest determined based on regenerated candidate tissue map. In this manner, various inefficiencies may be avoided, such as undesirably carrying out high resolution scanning based on original defective candidate tissue map, resulting in potentially performing high resolution scanning on the wrong regions of slide and/or missing regions that it would have been desirable to scan at high resolution. Additionally, one may avoid untimely detection of errors, such as detection of an error after slide has been removed from scanner 124 and placed back into storage, resulting in potentially significant delays and additional manual processing.

Continuing to reference FIG. 1, system 100 includes computing device 104. Computing device 104 includes processor 108 communicatively connected to memory 112. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 2:
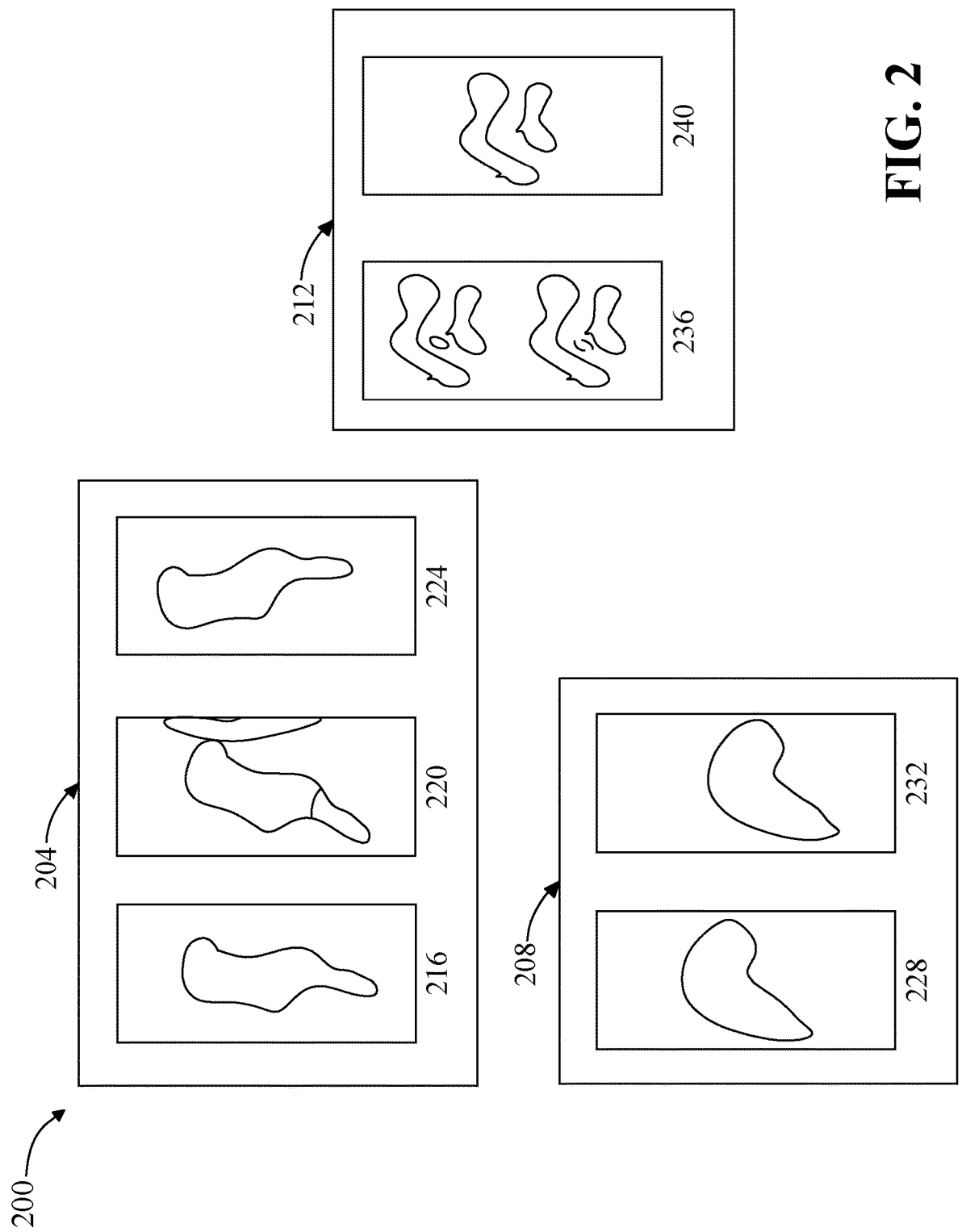
FIG. 2 is a simplified diagram illustrating different example serial sections, in accordance with some embodiments.

Now referring to FIG. 2, exemplary serial sections in various cases are shown. During the process of slide digitization, multiple serial sections may be assessed for a patient case and/or tissue block of a patient case. In this embodiment, these serial sections are therefore not independent from each other. Rather, the associations among these serial sections may give rise to patterns, trends, and/or other information that may be leveraged in the slide digitization process. For instance, such information can be utilized to correct a serial section under assessment which may have been contaminated.

With further reference to FIG. 2, first serial section set 204 and a second serial section set 208 may be related to a first patient case and thereby assigned a unique case identification number associated with the first patient case. The first serial section set 204 may be acquired from a first tissue block of the first patient case and the second serial section set 208 may be acquired from a second tissue block of the first patient case. Additionally, in some embodiments, a third serial section set 212 may be related to a second patient case and thereby assigned another unique case identification number associated with the second patient case. The third serial section set 212 may be acquired from a first tissue block of the second patient case. The first serial set 204 may include a first stain slide 216, a second stain slide 220, and a third stain slide 224. The second serial section set 208 may include a fourth stain slide 228 and a fifth stain slide 232. The third serial section set 212 may include a sixth stain slide 236 and a seventh stain slide 240.

Continuing to reference FIG. 2, in determining the first tissue block of the first patient case, the first stain slide 216 may be identified as a reference slide among the first serial section set 204 that may be used for the slide digitization process described in the present disclosure. In some examples, the first stain slide 216 identified as a reference slide may be an H&E-stained slide. When a group of slides are processed together, the reference slide may provide information for assessing other slides with other stains. For example, and without limitation, the second stain slide 220 and the third stain 224 slide may be utilized as candidate slides.

In further reference to FIG. 2, in some embodiments, a non-H&E-stained slide may be identified and used as a reference slide for processing a group of slides. For example, and without limitation, when determining the second tissue block of the first patient case, the second serial section set 208 is processed as a group for the slide digitization process described in the present disclosure. In the second serial section set 208, the fourth stain slide 228 may be a non-H&E-stained slide, which may be identified and used as a reference slide for assessing the fifth stain slide 232. The fifth stain slide 232 may be a candidate slide in the second serial section set 208.

Still referencing FIG. 2, in some embodiments, multiple serial sections may be placed on the same slide, which is referred to as an intra-serial section slide. For example, and without limitation, the sixth stain slide 236 in the third serial section set 212 is an intra-serial section slide. Alternatively, in embodiments that only one serial section is placed on a slide, the embodiment is referred to as an inter-serial section slide.

Figure 3:
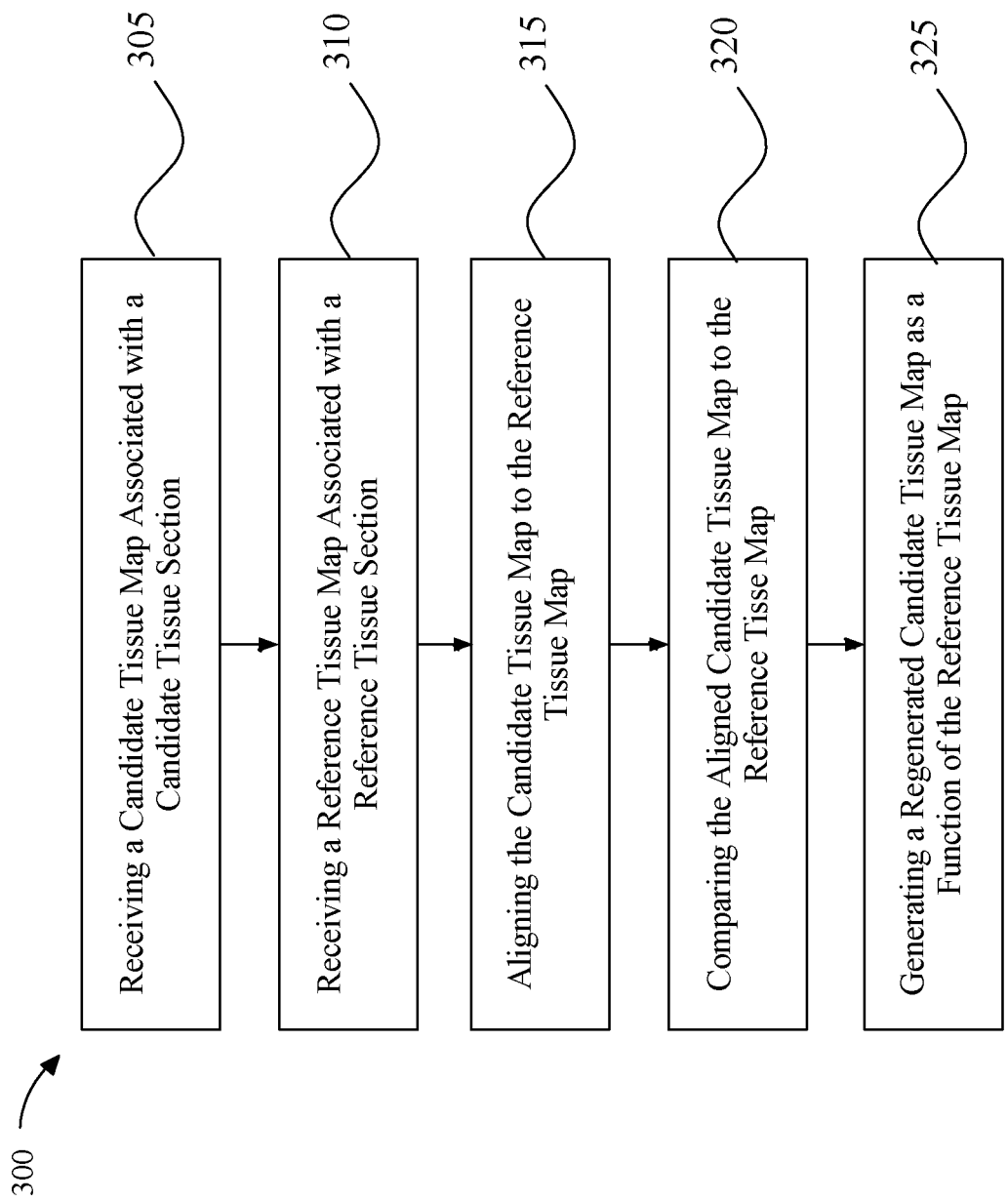
FIG. 3 is a flow chart illustrating an exemplary method for slide digitization, in accordance with some embodiments.

Now referring to FIG. 3, an exemplary method of digitization of tissue slides based on associations among serial sections may include receiving a candidate tissue map associated with a candidate tissue section 305, receiving a reference tissue map associated with a reference tissue section 310, aligning the candidate to the reference tissue map 315, comparing the aligned candidate tissue map to the reference tissue map 320, and generating a regenerated candidate tissue map as a function of the reference tissue map 325. The receipt of the candidate tissue map 304 and the reference tissue map 310 may flow from other methods and/or processes as described here within and/or from an independent process and/or method. These methods and/or processes may include other programs and or artificial intelligence programs configured to replicate the manual processing of slide analysis and/or digitization processes.

Continuing to reference FIG. 3, The alignment of the candidate tissue map to reference tissue map 315 may further generate a reference-aligned candidate tissue map. In some embodiments, the process of such alignment may apply image registration techniques. By aligning one or more features such as tissue boundaries and/or contours shared by the candidate tissue map and the reference tissue map, the registration is performed. Alignment may occur in two and/or three dimensions in order to maximize the overlap of common features shared by both maps. Common features may include features that are detectable in both tissue maps. For example, by way of automated computer vision techniques as described in further detail throughout this disclosure.

Further referencing FIG. 3, comparison of the aligned candidate tissue map to the reference tissue map 320 may further include generating a reference binary mask from the reference tissue map and a candidate binary mask from the candidate tissue map, aligning the reference binary mask and the candidate binary mase based on the results of the alignment process, adjusting the candidate binary mask based on the reference binary mask, resulting in a corrected binary mask, and applying the corrected candidate binary mask onto the candidate tissue map. This process facilitates comparison between substantially the same tissue-containing regions of the candidate tissue map and reference tissue map.

With further reference to FIG. 3, method 300 may include generating a regenerated candidate tissue map 325 based on the differences between the candidate tissue map and the reference tissue map identified within the comparison phase of the method. Otherwise stated as generating a regenerated candidate issue map as a function of the reference tissue map 325. The identified differences within the comparison phase may be used as correction factors to adjust the candidate tissue map.

Continuing to refer to FIG. 3, a method for digitization of tissue slides based on associations among serial sections may further include identifying a candidate serial section from at least one stain type, identifying a reference serial section, generating the reference tissue map in response to scanning the reference serial section, and generating the candidate tissue map in response to scanning the candidate serial section. In an embodiment, these additional methods and/or processes may be completed prior to receiving a candidate tissue map associated with the candidate tissue section. A candidate serial section may be identified based on stain information such as stain types. The candidate serial section is associated with identifying information such as a related pair of a case identification number and a block identification number. Likewise, a reference serial section may be identified based on identifying information such as the case identification number and the block identification number. In some embodiments, the candidate serial section and the reference serial section are on different slides. In other cases, the candidate serial section and the reference serial section are on the same slide. By identifying multiple sub-components on the same slide of repeating patterns, a slide with multiple serial sections may be identified. In some embodiments, the slides used for serial sections can be H&E slides, non-H&E slides, or any combination thereof. Generation of a reference tissue map in response to scanning the reference serial section may be accomplished by scanning the reference serial section with scanner and outputting a digitized slide. Likewise, generation of the candidate tissue map may occur through scanning of the candidate serial section resulting in another digitized slide. In some embodiments, based on aggregation of sub-components of a generated tissue map on a slide, the presence of a repeating pattern may indicate that multiple serial sections are present on the same slide. These processes, although stated in phased terms, may occur simultaneously and/or near simultaneously with other methods as described throughout this disclosure.

Figure 4:
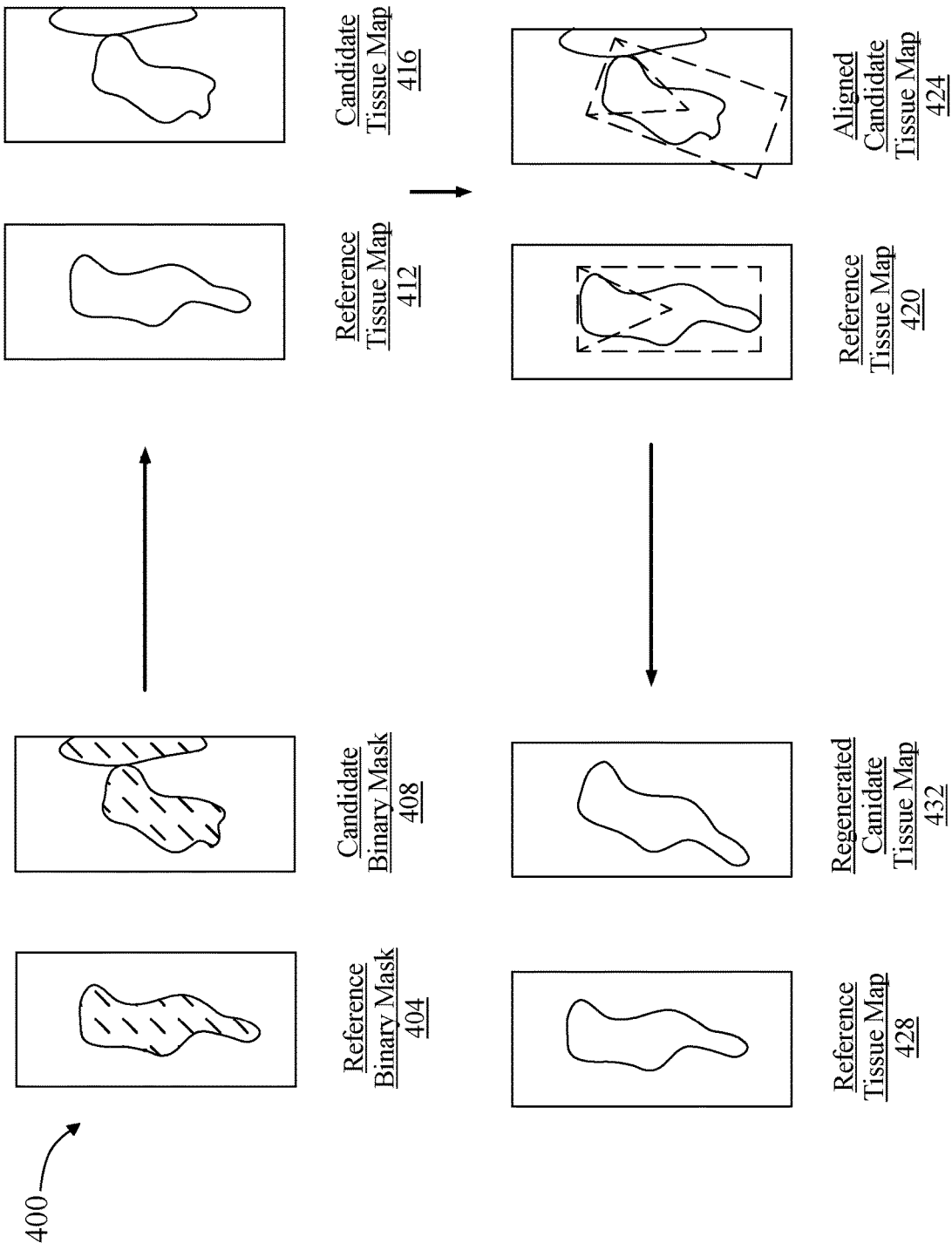
FIG. 4 is a simplified diagram illustrating serial sections on different slides at various stages during slide digitization, in accordance with some embodiments.

Now referring to FIG. 4, illustrated are serial sections on different slides at various stages during an exemplary process of slide digitization. Prior to generation of candidate tissue map 416 and reference tissue map 412, a candidate binary mask 408 and a reference binary mask 404 are resulted from the scanning of serial sections on their respective slides. The candidate binary mask 408 is initially wrongly assessed due to the presence of debris and/or lack of stain intensity of a portion of the tissue. Alternatively, the reference binary mask 404 appears to be correctly assessed of tissue shape and size by an inline automatic computer program. When the inline registration is completed, the candidate tissue map 416 is aligned with the reference tissue map 412. The reference binary mask 404 is used to correct the candidate binary mask 408. As a result, an aligned candidate tissue map 424 is generated. The aligned candidate tissue map 424, which is based on the corrected candidate binary mask 404, may then be used to regenerate the candidate tissue map. Following the process of regeneration of the candidate tissue map, the regenerated candidate tissue map 432 appears to represent tissue with similar shape and size as the reference tissue map 428. Alternatively, the orientation and the relative location on the glass slide appears to be different between the regenerated candidate tissue map 432 and the reference tissue map 428.

Figure 5:
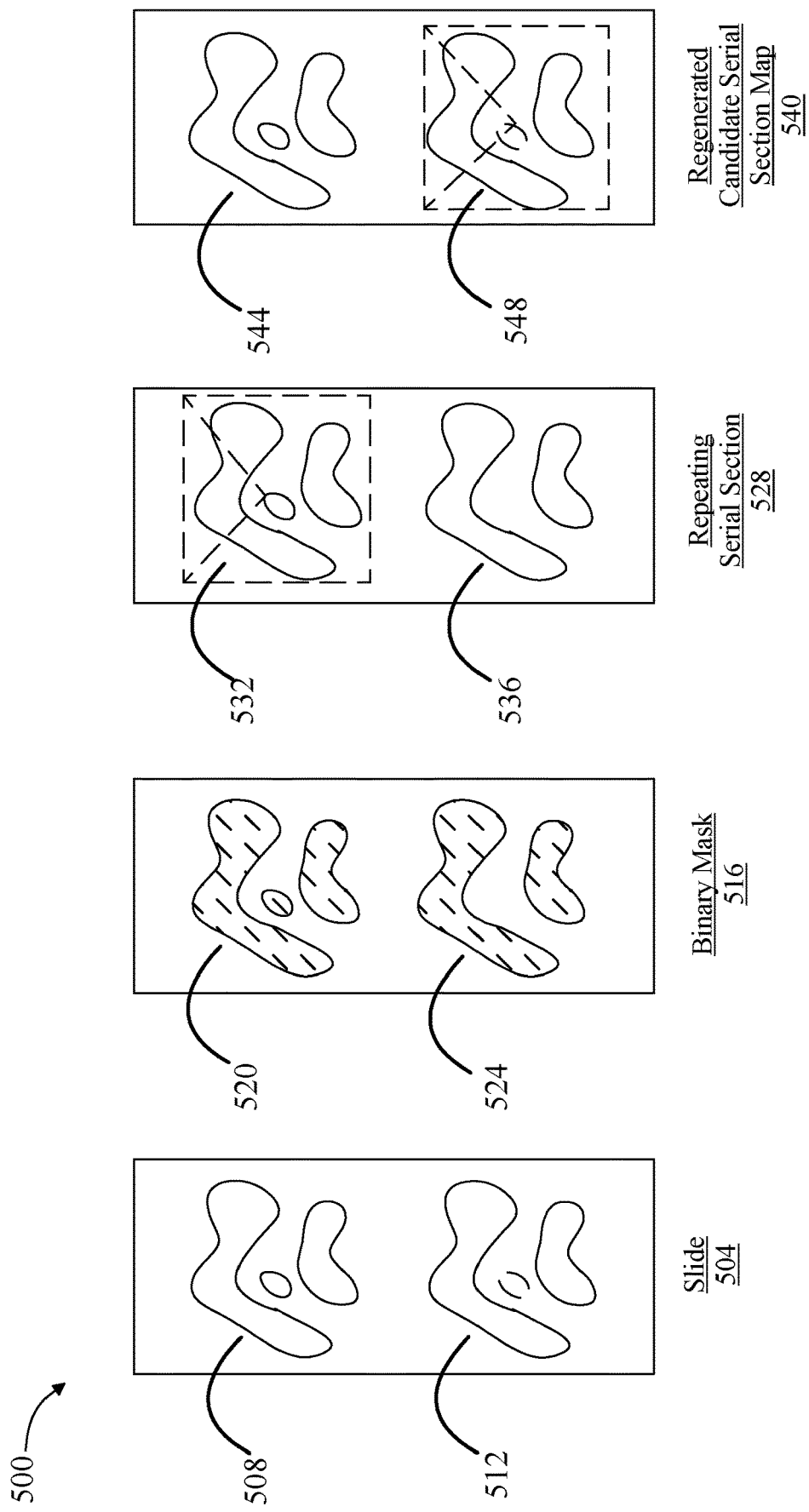
FIG. 5 is a simplified diagram illustrating serial sections on the same slide at various stages during slide digitization, in accordance with some embodiments.

Now referring to FIG. 5, illustrated is serial sections on the same slide at various stages during an example process of slide digitization, in accordance with some embodiments. In the illustrated example, an intra-serial section slides 504 may include a reference serial section 508 and a candidate serial section 512 on the same slide. An "intra-serial section slide," as used throughout this disclosure is a slide that has more than one serial section placed on it. The rest of the slides as illustrated include serial slides at various points of the method as described above and throughout this disclosure. An intra-serial binary mask section slide is shown and may include a binary mask of a reference serial section 520 and a candidate serial section 524 on the same slide. The repeating serial section 528 additionally may include a reference serial section 532 and a candidate serial section 536. Lastly, the regenerated candidate serial section map 540 may include a reference serial section 544 and a candidate serial section 548.

Continuing to reference FIG. 5, in some embodiments, no slide is manually labeled as an intra-seral section slide before the process of slide digitization. Instead, an inline registration process of an intra-serial section slide is performed by a processor with automatic computer programs. In the first phase of the registration of intra-serial section slide, the inline registration program finds all repeating matches of serial sections matching features of the reference template, such as shapes and/or sizes. In the second phase of the registration of intra-serial section slide, the inline registration program expands the reference template to be applied onto all matching serial sections found in the first phase. When completing the first phase and the second phase, the slide being assessed is registered as an intra-serial section slide.

With further reference to FIG. 5, the information about the count and location of serial sections on an intra-serial section slide may be utilized in the process of digitizing intra-serial section slide. In some embodiments, a user may input parameters and/or instructions regarding the count and location of serial sections through a user interface. In some embodiments, such information may be detected by an inline algorithm configured to identify and/or locate sub-sections of tissue and/or sub-components of serial sections having similarities. Executing the inline algorithm stored in a memory device, a processor assesses the content of every slide to determine whether there are repeated fragments present. In an embodiment where repeating fragments are present on a slide, they may be identified by the processor as an intra-serial sections slide. An intra-serial sections slide may also be referred to as an intra-serial fragment slide. The intra-serial section slide may be H&E-stained and/or non-H&E-stained.

Continuing to reference FIG. 5, during the process of digitizing an intra-serial section slide, one of the serial sections may be identified as a reference serial section. This determination may be determined by the processor by way of locating repeating patterns. Other serial sections on the same slide may then be checked against the reference serial section. In turn, the corresponding tissue maps are corrected in view of the reference serial section. In FIG. 5 specifically, a reference serial section is assessed by the processor to identify and recover the missing tissue fragment from a candidate serial section.

Figure 6:
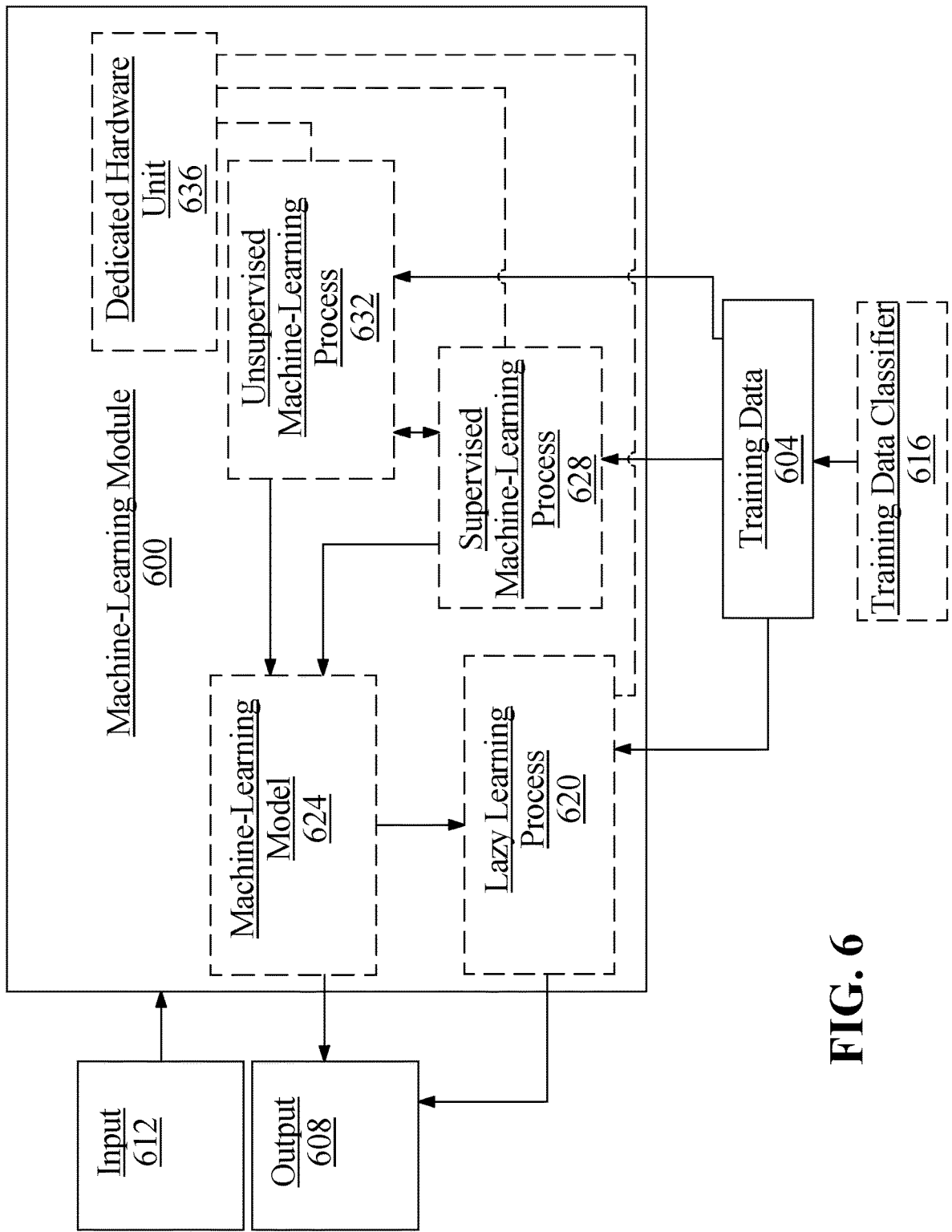
FIG. 6 is an exemplary embodiment of a machine learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example classification numbers, block numbers, serial section slides, candidate slide, reference slide, and/or any other additional training data as described throughout this disclosure.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to delineate between tissue data and other interfering factors, such as without limitation, extra stain, bubbles, and/or scratches on the slide.

Still referring to FIG. 6, computing device 604 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 604 may then calculate a likelihood table by calculating probabilities of different data entries and classification labels. Computing device 604 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 6, computing device 604 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 6, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 6, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 6, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 6, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25th percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 6, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

With continued reference to FIG. 6, in one or more embodiments, computing device may implement one or more aspects of "generative artificial intelligence (AI)," a type of AI that uses machine learning algorithms to create, establish, or otherwise generate data such as, without limitation, scanned slides data, regenerated slides data, and/or the like in any data structure as described herein (e.g., text, image, video, audio, among others) that is similar to one or more provided training examples. In an embodiment, machine learning module described herein may generate one or more generative machine learning models that are trained on one or more set of scanned slides data and/or regenerated slides data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 6, in some cases, generative machine learning models may include one or more generative models. As described herein, "generative models" refers to statistical models of the joint probability distribution P(X,Y) on a given observable variable x, representing features or data that can be directly measured or observed (e.g., digitized slides, scanned slides data, and/or the like) and target variable y, representing the outcomes or labels that one or more generative models aims to predict or generate (e.g., regenerated slides data and/or the like). In some cases, generative models may rely on Bayes theorem to find joint probability; for instance, and without limitation, Naïve Bayes classifiers may be employed by computing device to categorize input data such as, without limitation, scanned slides data into different classes, labels, cohorts, categories or the like such as, without limitation, true/false, correct/incorrect, and/or the like.

In a non-limiting example, and still referring to FIG. 6, one or more generative machine learning models may include one or more Naïve Bayes classifiers generated, by computing device, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing Device may then calculate a likelihood table by calculating probabilities of different data entries and classification labels. Computing device may utilize a naïve Bayes equation to calculate a posterior probability for each class. A class containing the highest posterior probability is the outcome of prediction.

Still referring to FIG. 2, although Naïve Bayes classifier may be primarily known as a probabilistic classification algorithm; however, it may also be considered a generative model described herein due to its capability of modeling the joint probability distribution P(X,Y) over observable variables X and target variable Y. In an embodiment, Naïve Bayes classifier may be configured to make an assumption that the features X are conditionally independent given class label Y, allowing generative model to estimate the joint distribution as $P(X,Y)=P(Y)\Pi_i P(X_i|Y)$, wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of regenerated slides data based on aligned tissue maps (e.g., candidate, reference, and/or aligned tissue maps), wherein the models may be trained using training data containing a plurality of features e.g., features of slides data, including candidate tissue maps, reference tissue maps, and/or aligned tissue maps, and/or the like as input correlated to a plurality of labeled classes e.g., correct/incorrect as output.

Still referring to FIG. 6, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 6.

With continued reference to FIG. 6, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 6 to distinguish between different categories e.g., real vs. fake, correct vs. incorrect, or similar pair of contradictory terms, or states e.g., TRUE vs. FALSE within the context of generated data such as, without limitations, regenerated slides data, and/or the like. In some cases, computing device may implement one or more classification algorithms such as, without limitation, Support Vector Machines (SVM), Logistic Regression, Decision Trees, and/or the like to define decision boundaries.

In a non-limiting example, and still referring to FIG. 6, generator of GAN may be responsible for creating synthetic data that resembles real regenerated slides data. In some cases, GAN may be configured to receive scanned slides data such as, without limitation, candidate tissue maps, reference tissue maps, and/or aligned tissue maps, as input and generates corresponding regenerated slides data containing information describing or evaluating the performance of one or more aligned tissue maps. On the other hand, discriminator of GAN may evaluate the authenticity of the generated content by comparing it to real regenerated slides data, for example, discriminator may distinguish between genuine and generated content and providing feedback to generator to improve the model performance.

With continued reference to FIG. 6, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 6, VAE may be used by computing device to model complex relationships between scanned slides data e.g., candidate tissue maps, reference tissue maps, and/or aligned tissue maps. In some cases, VAE may encode input data into a latent space, capturing regenerated slides data. Such encoding process may include learning one or more probabilistic mappings from observed scanned slides data to a lower-dimensional latent representation. Latent representation may then be decoded back into the original data space, therefore reconstructing the scanned slides data. In some cases, such decoding process may allow VAE to generate new examples or variations that are consistent with the learned distributions.

With continued reference to FIG. 6, in some embodiments, one or more generative machine learning models may be trained on a plurality of visual data as described herein, wherein the plurality of visual data may provide visual information that generative machine learning models analyze to understand the dynamics of digitized slides.

Additionally, or alternatively, one or more generative machine learning models may utilize one or more predefined templates representing, for example, and without limitation, correct regenerated slides data. In a non-limiting example, one or more templates, such as a regenerated slides data repository (i.e., predefined models or representations of correct and ideal regenerated slides data) may serve as benchmarks for comparing and evaluating plurality of scanned slides data.

Still referring to FIG. 6, computing device may configure generative machine learning models to analyze input data such as, without limitation, scanned slides data to one or more predefined templates such as regenerated slides data repository representing correct regenerated slides data described above, thereby allowing computing device to identify discrepancies or deviations from regenerated slides data. In some cases, computing device may be configured to pinpoint specific errors in candidate slides, reference slides, and/or aligned slides, or any other aspects of the scanned slides data. In a non-limiting example, computing device may be configured to implement generative machine learning models to incorporate additional models to detect discrepancies in scanned slides data and/or interfering factors such as scratches bubbles, and/or extra stain. In some cases, errors may be classified into different categories or severity levels. In a non-limiting example, some errors may be considered minor, and generative machine learning model such as, without limitation, GAN may be configured to generate regenerated slides data contain only slight adjustments while others may be more significant and demand more substantial corrections. In some embodiments, computing device may be configured to flag or highlight missed tissue areas, extra stain, scratches in the glass, and/or bubbles, altering the scanned slides data to reflect the actual tissue scan, directly on the scanned slides data using one or more generative machine learning models described herein. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 6, in some cases, computing device may be configured to identify, and rank detected common deficiencies (e.g. missed tissue area, bubbles, excess stain, scratches, and/or the like) across plurality of scanned slides data; for instance, and without limitation, one or more machine learning models may classify errors in a specific order e.g., excess stain, missed tissue, bubbles, and or scratches in a descending order of commonality. Such ranking process may enable a prioritization of most prevalent issues, allowing instructors or computing device to address the issue or deficiencies. In a non-limiting example, alignment of the candidate and reference tissue maps may allow computing device to regenerate a corrected tissue map.

Still referring to FIG. 6, in some cases, one or more generative machine learning models may also be applied by computing device to edit, modify, or otherwise manipulate existing data or data structures. In an embodiment, output of training data used to train one or more generative machine learning models such as GAN as described herein may include regenerated slides data that linguistically or visually demonstrate modified scanned slides data e.g., corrected scanned slides data that has missing and/or excess material/ tissue, and/or the like. In some cases, regenerated slides data may be synchronized with scanned slides data, for example, and without limitation, in alignment of the candidate tissue map and reference tissue map materials may be excluded and/or regenerated. Additionally, or alternatively, regenerated slides data may be generated using generative machine learning models to address the issue or deficiency in an alternative way. In some cases, such regenerated slides data may be integrated with the scanned slides data, offering user a multisensory instructional experience.

Additionally, or alternatively, and still referring to FIG. 6, computing device may be configured to continuously monitor scanned slides data. In an embodiment, computing device may configure discriminator to provide ongoing feedback and further corrections as needed to subsequent input data (e.g., candidate tissue map, reference tissue map, and/or aligned tissue map). In an embodiment, computing device may be configured to retrain one or more generative machine learning models based on regenerated slides data or update training data of one or more generative machine learning models by integrating additive or subtractive models into the original training data. In such embodiment, iterative feedback loop may allow machine learning module to adapt to the user's needs and performance, enabling one or more generative machine learning models described herein to learn and update based on regenerated slides data and generated feedback.

With continued reference to FIG. 6, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models may be used in the generation of regenerated slides data.

Still referring to FIG. 6, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate regenerated slides data. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models may be used to generate regenerated slides data that was formally missing or contained extra material described herein. As an ordinary person skilled in the art, upon reviewing the entirety of this disclosure, will be aware of various multi-model neural network and combination thereof that may be implemented by apparatus 100 in consistent with this disclosure.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described throughout this disclosure as inputs, outputs as described throughout this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 7:
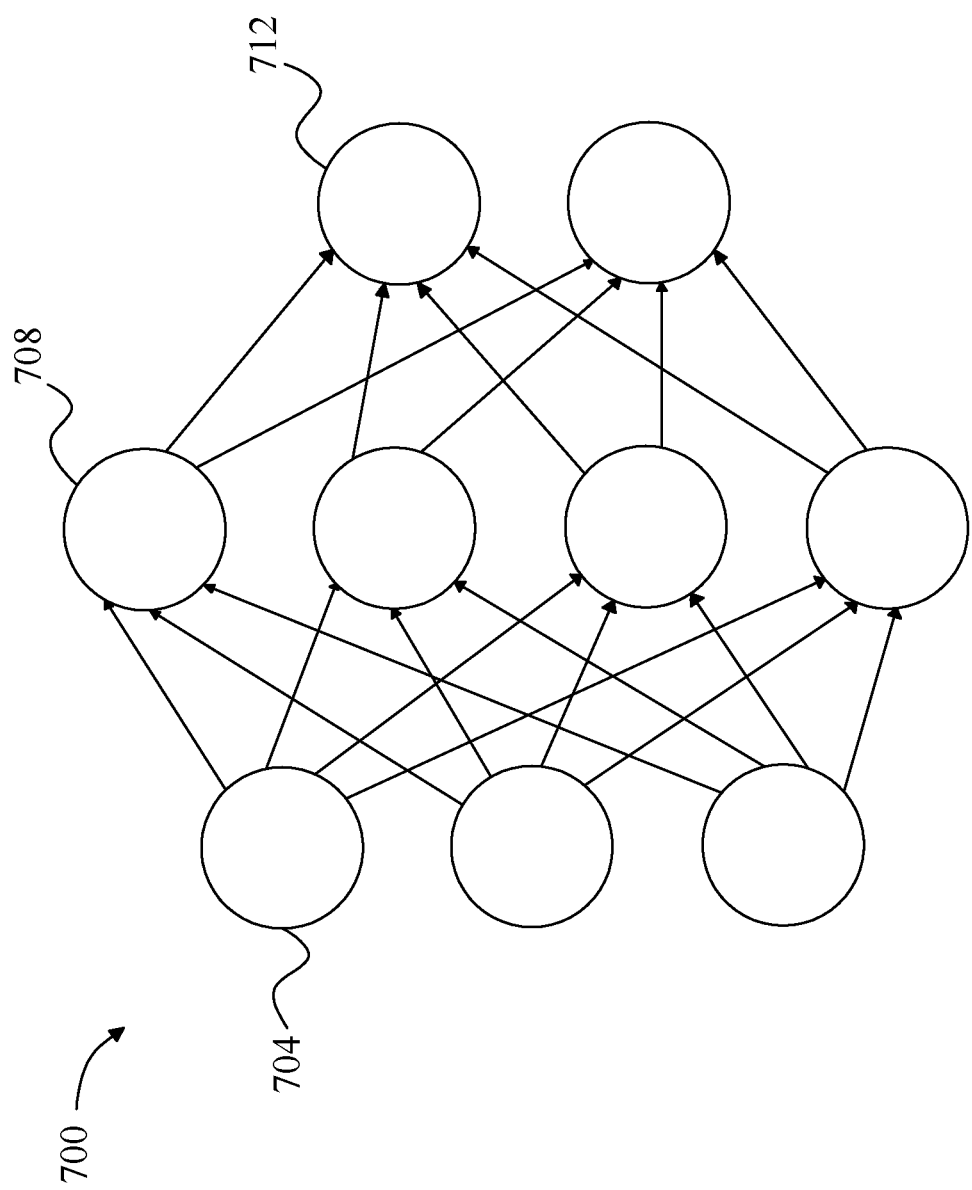
FIG. 7 is an exemplary embodiment of a neural network.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
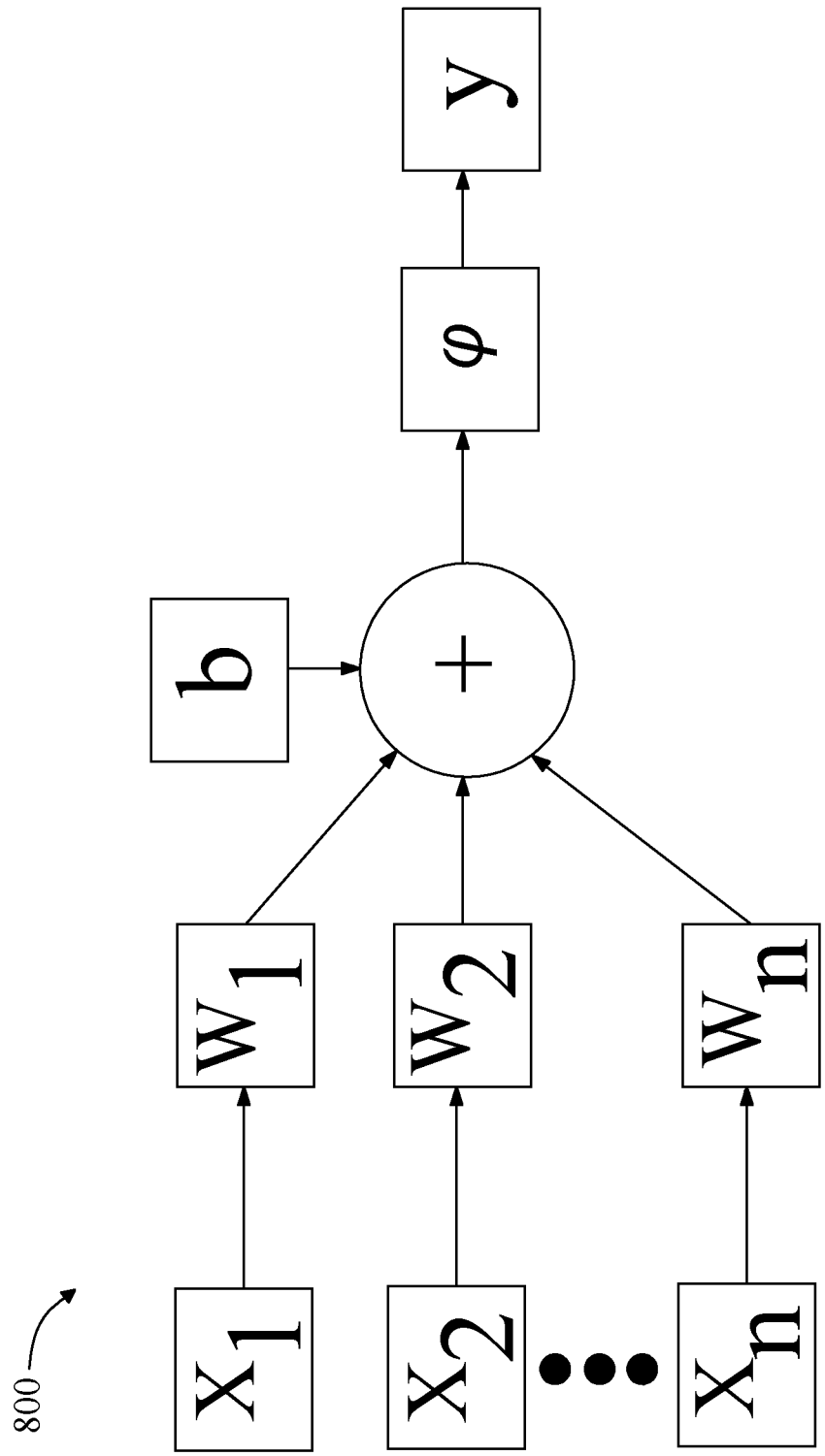
FIG. 8 is an exemplary embodiment of a node of neural network.

Referring now to FIG. 8, an exemplary embodiment of a node 800 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as f(x)=tanh²(x), a rectified linear unit function such as f(x)=max (0,x), a "leaky" and/or "parametric" rectified linear unit function such as f(x)=max (ax,x) for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as f(x)=x*sigmoid(x), a Gaussian error linear unit function such as f(x)=a(1+tanh($\sqrt{2/\pi}$(x+bx$^r$))) for some values of a, b, and r, and/or a scaled exponential linear unit function such as $$f(x) = \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
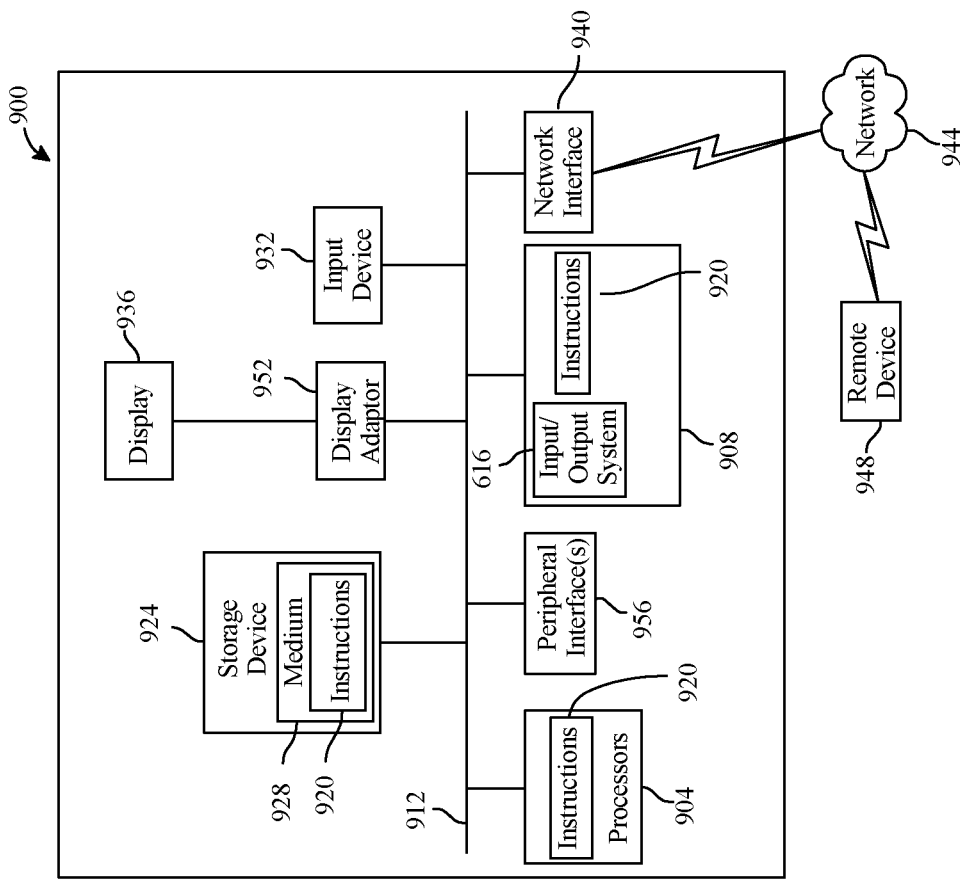
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for digitization of tissue slides based on associations among serial sections, wherein the system is comprised of:

at least a computing device, wherein the computing device is comprised of:
  a memory, wherein the memory stores instructions; and
  a processor, communicatively connected to the memory, wherein the processor is configured to:
    retrieve, from the memory, a candidate tissue map associated with a candidate tissue section, wherein the candidate tissue map is digital and comprises a digitized and then scanned slide at a high magnification wherein the scanned slide is restricted to content within an identified enclosing bounding box;
    retrieve a reference tissue map associated with a reference tissue section;
    align the candidate tissue map to the reference tissue map;
    compare the aligned candidate tissue map to the reference tissue map; and
    generate a regenerated candidate tissue map as a function of the reference tissue map, wherein the regenerated candidate tissue map is digital and generating the regenerated candidate tissue map comprises instantiating a machine learning module which further comprises:
      receiving training data, wherein the training data correlates a plurality of reference tissue map data to a plurality of regenerated candidate tissue map data;
      training, iteratively, the machine learning module using the training data, wherein training the machine learning module includes retraining the machine learning module with feedback from previous iterations of the machine learning module; and
      generating the regenerated candidate tissue map using the trained machine learning module; and
  a scanner, configured to scan a slide and send a digitized image of the slide to the computing device.

2. The system of claim 1, wherein the memory further includes instructions configuring the processor to:
  identify a candidate serial section from at least one stain type, wherein the candidate serial section is associated with a case identification number and a block identification number;
  identify a reference serial section based on the cane identification number and the block identification number;
  generate the reference tissue map in response to scanning the reference serial section; and
  generate the candidate tissue map in response to scanning the candidate serial section.

3. The system of claim 1, wherein the candidate serial section is on a first slide and the reference serial section is on a second slide.

4. The system of claim 1 wherein the candidate serial section and the reference serial section are both on a first slide.

5. The system of claim 1, wherein the system is further comprised of at least a storage device.

6. The system of claim 1, wherein the system is further comprised of a scanned slides data repository.

7. The system of claim 1, wherein the system is further comprised of a regenerated slides data repository.

8. The system of claim 1, wherein the system is further comprised of both a scanned slides data repository and a regenerated slides data repository.

9. The system of claim 1, wherein the system instantiates a machine learning module.

10. The system of claim 1, wherein the system instantiates a neural network.

11. A method for digitization of tissue slides based on associations among serial sections, wherein the method is comprised of:
  receiving, from a memory, a candidate tissue map associated with a candidate tissue section, wherein the candidate tissue map is digital and comprises a digitized and then scanned slide at a high magnification wherein the scanned slide is restricted to content within an identified enclosing bounding box;
  receiving a reference tissue map associated with a reference tissue section, the reference tissue section having a predetermined association with the candidate tissue section;
  aligning the candidate tissue map to the reference tissue map;
  comparing the aligned candidate tissue map to the reference tissue map; and
  generating a regenerated candidate tissue map as a function of the reference tissue map, wherein the regenerated candidate tissue map is digital and generating the regenerated candidate tissue map comprises instantiating a machine learning module which further comprises:
    receiving training data, wherein the training data correlates a plurality of reference tissue map data to a plurality of regenerated candidate tissue map data;
    training, iteratively, the machine learning module using the training data, wherein training the machine learning module includes retraining the machine learning module with feedback from previous iterations of the machine learning module; and
    generating the regenerated candidate tissue map using the trained machine learning module.

12. The method of claim 11, wherein the method further comprises:
  identifying a candidate serial section from at least one stain type, wherein the candidate serial section is associated with a case identification number and a block identification number;
  identifying a reference serial section based on the case identification number and the block identification number;
  generating the reference tissue map in response to scanning the reference serial section; and
  generating the candidate tissue map in response to scanning the candidate serial section.

13. The method of claim 11, wherein the candidate serial section is on a first slide and the reference serial section is on a second slide.

14. The method of claim 11, wherein the candidate serial section and the reference serial section are both on a first slide.

15. The method of claim 11, wherein the method further includes storage and retrieval of slides data from at least a storage device.

16. The method of claim 11, wherein the method further includes storage and retrieval of slides data from a scanned slides data repository.

17. The method of claim 11, wherein the method further includes storage and retrieval of slides data from a regenerated slides data repository.

18. The method of claim 11, wherein the method further includes storage and retrieval of slides data from both a scanned slides data repository and a regenerated slides data repository.

19. The method of claim 11, wherein the method instantiates a machine learning module.

20. The method of claim 11, wherein the method instantiates a neural network.

\* \* \* \* \*